United States Patent [19]

Wichman

[11] 4,275,720
[45] Jun. 30, 1981

[54] SURGICAL DRAPE WITH BARRIER MEMBER

[75] Inventor: Cynthia A. Wichman, St. Charles, Ill.

[73] Assignee: The Kendall Company, Boston, Mass.

[21] Appl. No.: 64,975

[22] Filed: Aug. 8, 1979

[51] Int. Cl.³ .................................................. A61F 13/00
[52] U.S. Cl. ....................................... 128/132 D; D24/49
[58] Field of Search .................... 206/440; 128/132 R, 128/132 D, 154, 155, 157, 292, 761, 767; D24/49

[56] References Cited

U.S. PATENT DOCUMENTS

| Re. 26,759 | 1/1970 | Melges | 128/292 |
| 3,835,851 | 9/1974 | Villari | 128/132 D |
| 3,871,369 | 3/1975 | Krzewinski | 128/132 D |
| 3,930,497 | 1/1976 | Krebs et al. | 128/132 D |
| 4,169,472 | 10/1979 | Morris | 128/132 D |

FOREIGN PATENT DOCUMENTS 2601124  7/1977  Fed. Rep. of Germany ........... 128/292

Primary Examiner—Robert W. Michell
Assistant Examiner—J. L. Kruter
Attorney, Agent, or Firm—Powell L. Sprunger

[57] ABSTRACT

A surgical drape comprising, a sheet of flexible material for covering a portion of a patient's body, a fenestration, first and second flaps on opposed sides of the fenestration and defining openings facing toward the fenestration, and a third flap spaced from the fenestration and connecting the first and second flaps, with the third flap defining an opening facing toward the fenestration.

20 Claims, 11 Drawing Figures

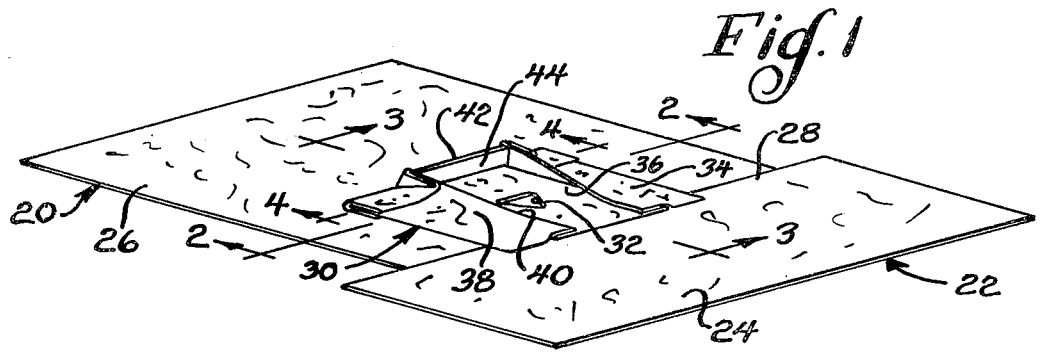
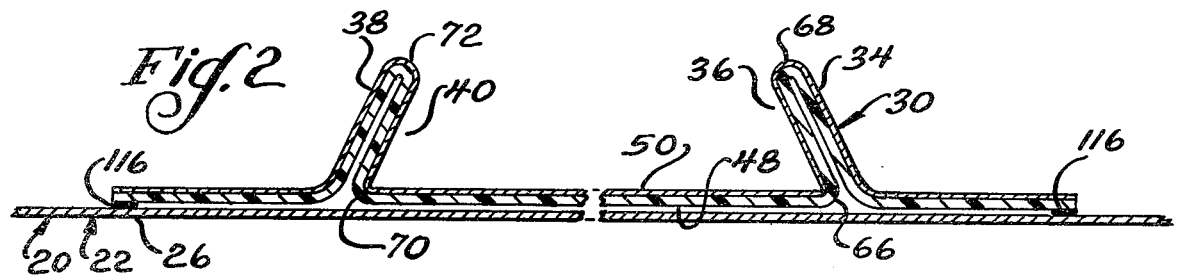
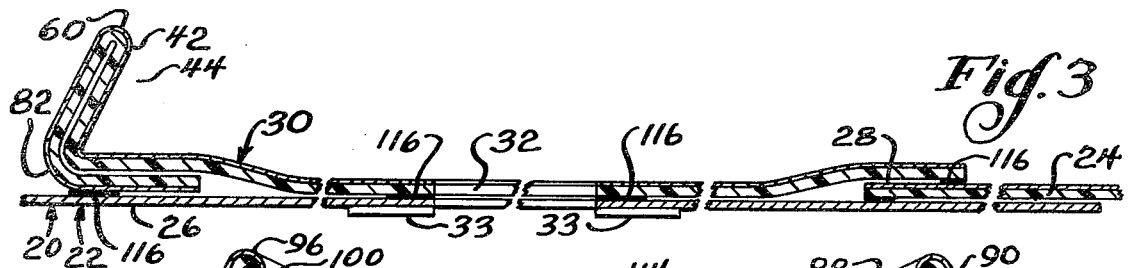
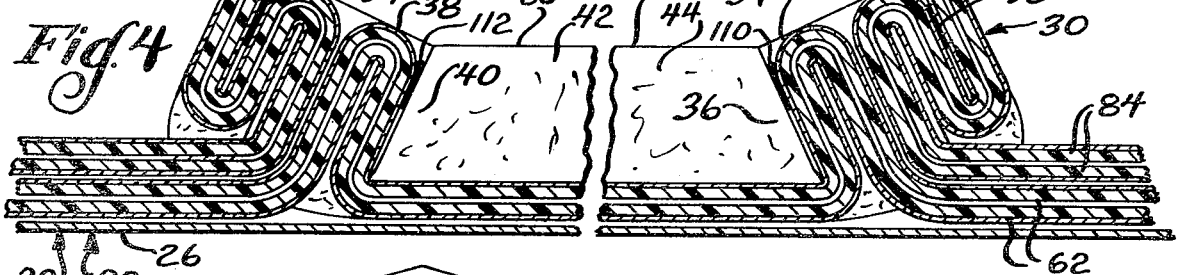
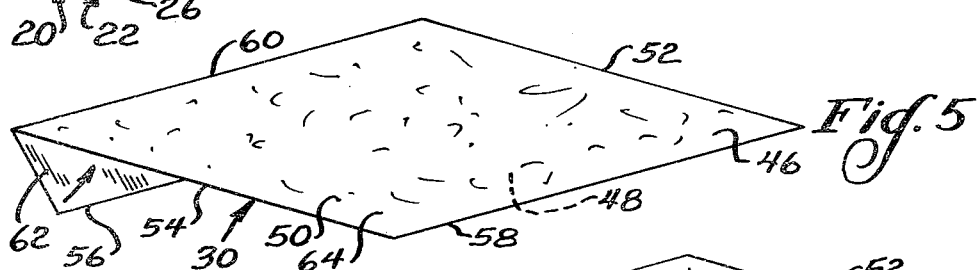
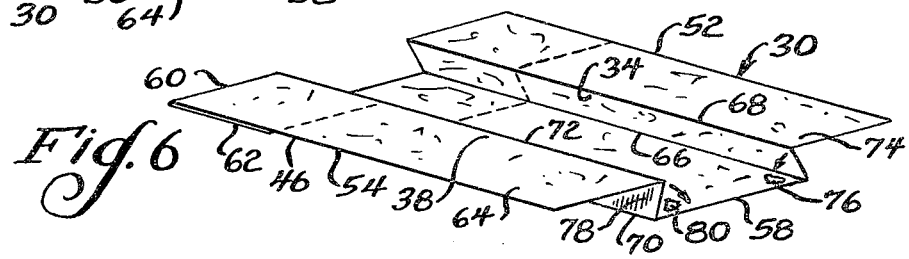

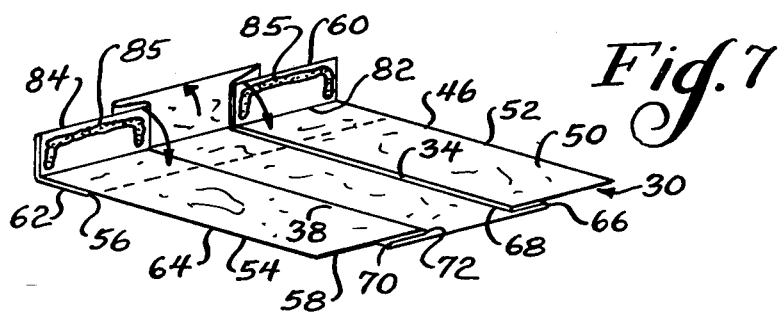
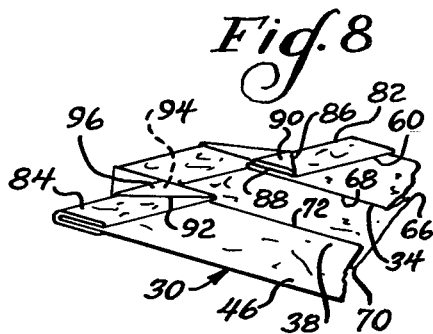
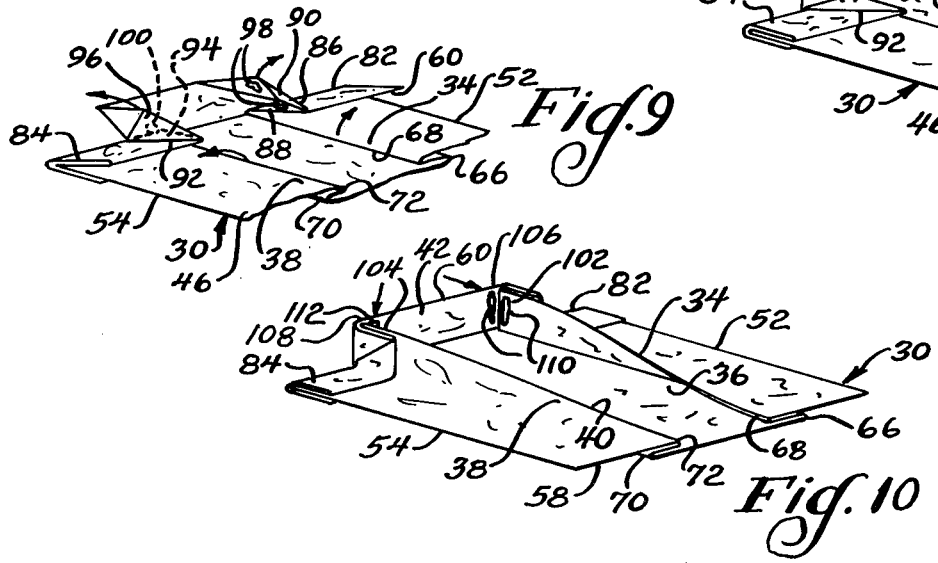
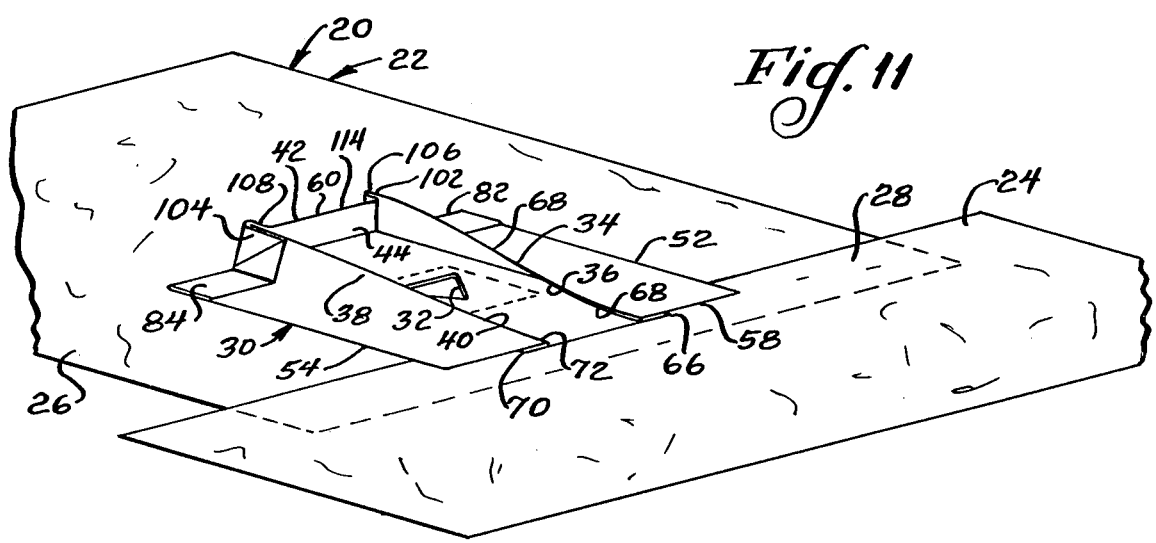

SURGICAL DRAPE WITH BARRIER MEMBER

BACKGROUND OF THE INVENTION

The present invention relates to articles of surgical apparel, and more particularly to surgical drapes.

Surgical drapes are normally constructed from a sheet of flexible material for placement over the body of a patient with a fenestration in the drape located at the site of the surgical procedure. During surgery, body fluids pass through the fenestration and over the outer surface of the drape, and, if unchecked, the fluids pass onto the floor or the garments of hospital personnel, such as the surgeon. In U.S. Pat. No. 3,791,382, incorporated herein by reference, it has been proposed to capture the runoff fluid in pockets of a drape. However, during certain surgical procedures, such as a cesarean operation, an excessive amount of fluid may pass through the fenestration, and the fluids may spread in multiple directions due to the location of the drape on the patient.

SUMMARY OF THE INVENTION

A principal feature of the present invention is the provision of an improved surgical drape.

The drape of the present invention comprises, a sheet of flexible material for covering a portion of a patient's body, a fenestration, first and second flaps on opposed sides of the fenestration and defining openings facing toward the fenestration and a third flap spaced from the fenestration and connecting the first and second flaps, with the third flap defining an opening facing toward the fenestration.

A feature of the present invention is that the flaps of the drape are capable of capturing an excessive amount of body fluids which may pass through the fenestration. Another feature of the invention is that the flaps capture body fluids spreading from the fenestration in multiple directions along the outer surface of the drape.

Yet another feature of the invention is that the third flap is connected to ends of the first and second flaps in a manner such that the flaps are maintained in a partially upright position to assure that the connected flaps provide a fluid barrier around three sides of the fenestration.

Still another feature of the invention is that the flaps are constructed from a single piece of material to prevent leakage.

Further features will become more fully apparent in the following description of the embodiments of this invention and from the appended claims.

DESCRIPTION OF THE DRAWINGS

In the drawings:

FIG. 1 is a perspective view of a surgical drape of the present invention;

FIG. 2 is a fragmentary sectional view taken substantially as indicated along the line 2—2 of FIG. 1;

FIG. 3 is a fragmentary sectional view taken substantially as indicated along the line 3—3 of FIG. 1;

FIG. 4 is a fragmentary sectional view taken substantially as indicated along the line 4—4 of FIG. 1;

FIGS. 5-10 are perspective views illustrating folding steps during formation of a barrier member for the drape of FIG. 1; and FIG. 11 is a fragmentary perspective view of the drape constructed in accordance with the steps of FIGS. 5-10.

DESCRIPTION OF THE PREFERRED EMBODIMENTS

Referring now to FIGS. 1-4, there is shown a surgical drape generally designated 20 having a main sheet 22 comprising first and second segments 24 and 26, which are secured together in a suitable manner, such as by adhesive, in a region 28 where edges of the segments 24 and 26 overlap. The drape 20 also has a barrier member 30 which serves as a reinforcement sheet for the main sheet 22, with the barrier member 30 and main sheet 22 having a fenestration 32 extending therethrough, with the fenestration 32 preferably having the general shape of an isosceles triangle for particular surgical procedures, such as a cesarean operation. If desired, the main sheet 22 may have a region 33 of adhesive surrounding the fenestration on a lower surface of the main sheet 22 for securement to the patient. As shown, the barrier member 30 has a first elongated flap 34 on one side of the fenestration 32 defining a first opening 36 facing toward the fenestration 32, a second flap 38 on the opposed side of the fenestration 32 relative to the first flap 34 and defining a second opening 40 facing toward the fenestration 32, and a third flap 42 spaced from the fenestration 32 and extending between the first and second flaps 34 and 38, respectively, with the third flap 42 defining a third opening 44 facing toward the fenestration 32. As will be discussed below, the first, second, and third flaps 34, 38, and 42, respectively, cooperate to maintain the flaps in at least a partially upright position adjacent the juncture of the third flap 42 with the first and second flaps 34 and 38, respectively. As shown, the base of the triangular shaped fenestration 32 may face toward the third flap 42. The main sheet 22 and barrier member 30 may be constructed of suitable flexible material, such as a nonwoven material or a lamination having an outer sheet of nonwoven material and an inner sheet of fluid impervious material, such as plastic.

With reference to FIG. 5, the barrier member 30 of the drape 20 is constructed from a sheet 46 of flexible material, as described in the following manner. The sheet 46 has a first lower surface 48 for facing toward the patient after placement of the drape 20, a second upper surface 50 for facing away from the patient after placement of the drape, a pair of opposed first and second side edges 52 and 54, respectively, a pair of opposed first and second end edges 56 and 58, respectively, connecting the side edges 52 and 54. As shown, the sheet 46 has a first fold line 60 extending between the side edges 52 and 54, and defining a first section 62 extending between the first fold line 60 and the first end edge 56, and defining a second section 64 extending between the first fold line 60 and the second end edge 58. The first section 62 is folded beneath the second section 64 with the first surface 48 of the first section 62 facing the first surface 48 of the second section 64.

With reference to FIG. 6, the sheet 46 has a pair of generally aligned second and third fold lines 66 and 68, respectively, extending between the first fold line 60 and the second end edge 58, such that the second and third fold lines 66 and 68, respectively, define the first flap 34 with the third fold line 68 defining an outer edge of the first flap 34. The sheet 46 also has a pair of generally aligned fourth and fifth fold lines 70 and 72, respectively, extending between the first fold line 60 and the second end edge 58, and defining the second flap 38 with the fifth fold line 72 defining an outer edge of the second flap 38, and with the sheet 46 being folded such that the third fold line 68 is directed toward and spaced from the fifth fold line 72. As shown, a first end portion 74 of the first flap 34 adjacent the second end edge 58 may be secured to the underlying portion of the second sheet section 64 by suitable means 76, such as adhesive, in order to close the first flap 34 in the region of the first end portion 74 at the second end edge 58. Also, a second end portion 78 of the second flap 38 adjacent the second end edge 58 may be secured to the underlying portion of the second sheet section 64 by suitable means 80, such as adhesive, in order to close the second flap 38 in the region of the second end portion 78 at the second end edge 58.

With reference to FIG. 7, the sheet 46 has a sixth fold line 82 of the first and second sections 62 and 64, respectively, intermediate the first fold line 60 and the first end edge 56, with the sixth fold line 82 extending between the side edges 52 and 54, and with the sixth fold line 82 defining a third section 84 extending between the first fold line 60 and the sixth fold line 82. As shown, the third section 84 is folded over the second surface 50 of the second section 64 with the first fold line 60 facing toward the second end edge 58. In a preferred form, the sheet 46 has securing means 85, such as lines of adhesive, intermediate the third section 84 and the underlying portion of the sheet 46, with a portion of the securing means 85 being located intermediate the fifth fold line 72 and second side edge 54, and with a portion of the securing means 85 being located intermediate the third fold line 68 and the first side edge 52.

With reference to FIGS. 8 and 9, the sheet 46 has a seventh fold line 86 of the third section 84 extending between the juncture of the first and third fold lines 60 and 68, respectively, to the juncture of the second and sixth fold lines 66 and 82, respectively, and defining a first generally triangular section 88 defined by the third, sixth, and seventh fold lines 68, 82, and 86, respectively, and a second generally triangular section 90 overlying the first triangular section 88 defined by the first, second, and seventh fold lines 60, 66, and 86, respectively. The sheet 46 also has an eighth fold line 92 of the third section 84 extending between the juncture of the first and fifth fold lines 60 and 72, respectively, to the juncture of the fourth and sixth fold lines 70 and 82, respectively, and defining a third generally triangular section 94 defined by the fifth, sixth, and eighth fold lines 72, 82, and 92, respectively, and a fourth generally triangular section 96 overlying the third triangular section 94 and defined by the first, fourth, and eighth fold lines 60, 70, and 92, respectively. With reference to FIG. 9, the first triangular section 88 may be secured to the second triangular section 90 by suitable means 98, such as a line of adhesive. Similarly, the third triangular section 94 may be secured to the fourth triangular section 96 by suitable means 100, such as a line of adhesive.

After the triangular sections have been secured together, as discussed, and the first and second flaps 34 and 38 are raised in the manner illustrated in FIG. 10, the third flap 42 is formed extending between the first and second flaps 34 and 38, respectively. With reference to FIGS. 7-10, the second and fourth fold lines 66 and 70, respectively, in the third section 84 define opposed ends of the third flap 42, with the third flap 42 extending between the first and sixth fold lines 60 and 82, respectively, and extending between the second fold line 66 of the first flap 34 and the fourth fold line 70 of the second flap 38, with the first fold line 60 defining an outer edge of the third flap 42.

As best shown in FIG. 10, the first flap 34 has a third end portion 102 adjacent the sixth fold line 82 in the third section 84, and the second flap 38 has a fourth end portion 104 adjacent the sixth fold line 82 in the third section 84. As shown, the outer edges 68, 72, and 60, defined by the fold lines of the first, second, and third flaps 34, 38, and 42, respectively, are generally aligned in the folded configuration. The third flap 42 has a fifth end portion 106 located adjacent the juncture of the first and third flaps 34 and 42, respectively, and a sixth end portion 108 located adjacent the juncture of the second and third flaps 38 and 42, respectively. With reference to FIGS. 10 and 11, the fifth end portion 106 of the third flap 42 is secured to the third end portion 102 of the first flap 34 by suitable means 110, such as one or more lines of adhesive on these end portions. In the secured configuration, the outer edge 60 of the fifth end portion 106 extends a distance along the outer edge 68 of the third end portion 102, such that the secured fifth end portion 106 is generally tapered from the juncture of the second and sixth fold lines 66 and 82, respectively, to the outer edge 60 of the fifth end portion 106. Similarly, the sixth end portion 108 of the third flap 42 is secured to the fourth end portion 104 of the second flap 38 by suitable means 112, such as one or more lines of adhesive on the end portions 104 and 108. As shown, the outer edge 60 of the sixth end portion 108 extends a distance along the outer edge 72 of the fourth end portion 104, with the sixth end portion 108 of the third flap 42 being generally tapered from the juncture of the fourth and sixth fold lines 70 and 82, respectively, to the outer edge 60 of the sixth end portion 108.

With reference to FIGS. 2, 3, and 11, the barrier member 30 may be secured to the outer surface of the main sheet by suitable means 116, such as lines of adhesive, and the fenestration 32 may be formed through the barrier member 30 and main sheet 22. With reference to FIG. 11, the secured end portions of the first, second, and third flaps 34, 38, and 42, respectively, serve to define an intermediate outer edge portion 114 of the third flap 42 extending between the first and second flaps 34 and 38 with a length less than the distance between the second and fourth fold lines 66 and 70, respectively, along the sixth fold line 82 at the base of the third flap 42. In this manner, the secured end portions of the first, second, and third flaps 34, 38, and 42, respectively, maintain the flaps in a partially upright position adjacent the juncture of the third flap 42 and the first flap 34 and adjacent the juncture of the third flap 42 and the second flap 38. Thus, during use of the drape, the first, second, and third flaps 34, 38, and 42, respectively, are maintained in the raised position adjacent the third flap 42 in order to capture an excessive amount of body fluids which spread in multiple directions from the fenestration 32. Thus, for example, when the drape 20 is utilized during a cesarean procedure, the second drape segment 26 is placed between the patient's legs with the third flap 42 being located at a position lower than the fenestration 32 in the drape, such that body fluids pass outwardly from the fenestration 32 and spread in a general direction toward the third flap 42, with the raised first, second, and third flaps 34, 38, and 42, respectively, capturing and preventing passage of the fluids past the third flap 42 onto the floor or the physician.

The foregoing detailed description is given for clearness of understanding only, and no unnecessary limitations should be understood therefrom, as modifications will be obvious to those skilled in the art.

I claim:

1. A surgical drape, comprising: a sheet of flexible material for covering a portion of a patient's body, a fenestration, first and second flaps on opposed sides of the fenestration and defining openings facing toward the fenestration, and a third flap spaced from the fenestration and integrally connecting the first and second flaps such that it acts as one piece, said third flap defining an opening facing toward the fenestration.

2. The drape of claim 1 wherein said third flap is connected to the first and second flaps adjacent one end thereof.

3. The drape of claim 2 wherein the other ends of the first and second flaps are closed.

4. The drape of claim 1 including means for maintaining said third flap and portions of said first and second flaps adjacent said third flap in at least a partially upright position.

5. The drape of claim 1 wherein said third flap includes an outer free edge portion extending between the first and second flaps, and in which the length of said outer edge portion is less than the length of a lower portion of the third flap.

6. The drape of claim 5 wherein said third flap includes opposed end portions secured to said first and second flaps at a location remote said outer edge relative to said fenestration.

7. The drape of claim 6 wherein said end portions of said third flap have a generally triangular shape with outer sides of the triangular end portions extending along outer portions of said first and second flaps.

8. The drape of claim 1 wherein said third flap includes opposed end portions secured to said first and second flaps at a location remote the third flap opening relative to said fenestration.

9. The drape of claim 1 wherein said first flap includes a first outer edge, said second flap includes a second outer edge, and said third flap includes a third substantially free outer edge.

10. The drape of claim 9 wherein a substantial portion of said third edge is spaced from ends of said first and second edges.

11. The drape of claim 9 wherein said first, second, and third edges are generally aligned.

12. The drape of claim 9 wherein said third edge includes opposed end portions extending along said first and second edges, and in which said third edge includes an intermediate portion extending between inner ends of said end edge portions.

13. The drape of claim 9 wherein said first and second flaps include generally aligned ends adjacent one end of the first and second flaps, and said third flap includes opposed ends, with an end portion of said third flap adjacent one of its ends being secured to an end portion of said first flap adjacent the one end of the first flap, with an end portion of said third flap adjacent the other of its ends being secured to an end portion of said second flap adjacent the one end of the second flap, and with said end portions of the third flap being generally tapered defining a greater length of the end portions adjacent the outer edge of the third flap, such that said outer edge of the third flap intermediate the first and second flaps is located generally nearer the fenestration than the remainder of the third flap.

14. The drape of claim 1 wherein said fenestration has the general shape of an isosceles triangle with the base of said triangle facing toward the third flap.

15. A surgical drape, comprising: a sheet of flexible material having a first surface for facing toward the patient after placement of the drape, a second surface for facing away from the patient after placement of the drape, a pair of opposed first and second side edges, a pair of opposed first and second and edges connecting said side edges, a first fold line extending between said side edges and defining a first section extending between said first fold line and said first end edge, and a second section extending between said first fold line and said second end edge, said first section being folded beneath said second section with the first surface of the first section facing the first surface of the second section, a pair of generally aligned second and third fold lines extending between said first fold line and the second end edge defining a first flap with said third fold line defining an outer edge of said first flap, a pair of generally aligned fourth and fifth fold lines extending between said first fold line and the second end edge defining a second flap with said fifth fold line defining an outer edge of the second flap, with the outer edges of the first and second flaps being directed toward and spaced from each other, and with respective first and second end portions of the first and second flaps adjacent said second end edge being secured to the underlying portions of said second section to close said first and second flaps adjacent said second end edge, a sixth fold line of the first and second sections intermediate said first fold line and said first end edge, and extending between said side edges, said sixth fold line defining a third section extending between said first fold line and the sixth fold line, said third section being folded over the second surface of the second section with the first fold line facing toward the second end edge, a seventh fold line of the third section extending between the juncture of the first and third fold lines to the juncture of the second and sixth fold lines and defining a first generally triangular section defined by the third, sixth, and seventh fold lines, and a second generally triangular section overlying the first triangular section defined by said first, second, and seventh fold lines, an eighth fold line of the third section extending between the juncture of the first and fifth fold lines to the juncture of the fourth and sixth fold lines and defining a third generally triangular section defined by the fifth, sixth, and eighth fold lines, and a fourth generally triangular section overlying the third triangular section and defined by the first, fourth, and eighth fold lines, said second and fourth fold lines in said third section defining opposed ends of a third flap extending between said first and sixth fold lines and extending between the second fold line of the first flap and the fourth fold line of the second flap, with said first fold line defining an outer edge of the third flap, with said first flap having a third end portion adjacent the sixth fold line in the third section, with said second flap having a fourth end portion adjacent the sixth fold line in the third end section, and with the outer edges of the first, second, and third flaps being generally aligned, said third flap having a fifth end portion adjacent the juncture of the first and third flaps, said fifth end portion facing and being secured to the third end portion of the first flap, with the outer edge of said fifth end portion extending a distance along the outer edge of said third end portion, and with said fifth end portion being generally tapered from the juncture of the second and sixth fold lines to the outer edge of the fifth end portion, and said third flap having a sixth end portion adjacent the juncture of the second and third flaps, said sixth end portion facing and being secured to the fourth end portion of the second flap, with the outer edge of the sixth end portion extending a distance along the outer edge of said fourth end portion, and with said sixth end portion being generally tapered from the juncture of the fourth and sixth fold lines to the outer edge of the sixth end portion, said secured third and fifth end portions and secured fourth and sixth end portions maintaining the first, second, and third flaps in at least a partially upright position adjacent the juncture of the third flap with the first and second flaps, and defining an intermediate portion of the third flap outer edge extending between the outer edges of the first and second flaps and having a length less than the distance between the second and fourth fold lines.

16. The drape of claim 15 including a fenestration located intermediate said third and fifth fold lines and intermediate said sixth fold line and said second end edge.

17. The drape of claim 15 wherein said first triangular section is secured to said second triangular section, and in which said third triangular section is secured to said fourth triangular section.

18. The drape of claim 15 wherein the first surface of said folded sheet is secured to a surface of main sheet means.

19. The drape of claim 18 including a fenestration extending through said folded sheet and main sheet means, said fenestration being located intermediate said third and fifth fold lines of the folded sheet and intermediate the first fold line and second end edge of the folded sheet.

20. The drape of claim 15 including means for securing the third section to the underlying portion of the sheet, with a portion of the securing means being located intermediate the fifth fold line and the second side edge, and with a portion of the securing means being located intermediate the third fold line and the first side edge.

* * * * *